(12) United States Patent
Woo et al.

(10) Patent No.: US 12,265,044 B2
(45) Date of Patent: Apr. 1, 2025

(54) METHOD FOR DETECTING VOID IN CONCRETE COMPOSITE MEMBER COVERED WITH STEEL PLATE USING THERMAL IMAGE, AND METHOD FOR MANAGING CONSTRUCTION OF CONCRETE COMPOSITE MEMBER COVERED WITH STEEL PLATE BY APPLYING SAME

(71) Applicants: SAMSUNG C & T CORPORATION, Seoul (KR); KOREA HYDRO & NUCLEAR POWER CO., LTD., Gyeongju-si (KR)

(72) Inventors: Kyung Hun Woo, Suwon-si (KR); Woo Jin Cho, Seoul (KR); Jae Bog Lee, Gyeongju-si (KR); Sang Joon Park, Sacheon-si (KR); Ji Yong Yu, Seoul (KR); Tae Ha Park, Seoul (KR); Hyun Il Park, Gyeonggi-do (KR); Chang Gook Song, Busan (KR); Jhin Woo Shin, Seongnam-si (KR)

(73) Assignees: SAMSUNG C & T CORPORATION, Seoul (KR); KOREA HYDRO & NUCLEAR POWER CO., LTD., Gyeongju-si (KR)

( * ) Notice: Subject to any disclaimer, the term of this patent is extended or adjusted under 35 U.S.C. 154(b) by 601 days.

(21) Appl. No.: 17/622,562

(22) PCT Filed: Jun. 17, 2020

(86) PCT No.: PCT/KR2020/007832
§ 371 (c)(1),
(2) Date: Dec. 23, 2021

(87) PCT Pub. No.: WO2020/262878
PCT Pub. Date: Dec. 30, 2020

(65) Prior Publication Data
US 2022/0268719 A1    Aug. 25, 2022

(30) Foreign Application Priority Data
Jun. 26, 2019 (KR) .................... 10-2019-0076336

(51) Int. Cl.
*G01N 25/72* (2006.01)
*G01J 5/02* (2022.01)
(Continued)

(52) U.S. Cl.
CPC .............. *G01N 25/72* (2013.01); *G01J 5/027* (2013.01); *G01K 3/08* (2013.01); *G01N 33/383* (2013.01); *G01J 2005/0077* (2013.01)

(58) Field of Classification Search
None
See application file for complete search history.

(56) References Cited

U.S. PATENT DOCUMENTS

2015/0284916 A1* 10/2015 Dworsky .............. E01C 11/005
404/95

FOREIGN PATENT DOCUMENTS

CN       108444936 A   *  8/2018  ............... G01J 5/00
GB       2 309 077          7/1997
(Continued)

OTHER PUBLICATIONS

International Search Research, with English translation, for International Application No. PCT/KR2020/007832, dated Sep. 18, 2020.
(Continued)

*Primary Examiner* — Erica S Lin
(74) *Attorney, Agent, or Firm* — KILE PARK REED & HOUTTEMAN PLLC (57) ABSTRACT

The present invention relates to a method for detecting a void in a concrete composite member covered with a steel plate using a thermal image, and a method for managing the
(Continued)

construction of a concrete composite member covered with a steel plate by applying same. According to the present invention, since the presence of the void is determined based on the steel plate surface temperature measured using the thermal image during the construction of the concrete composite member covered with the steel plate, the void generation may be precisely expected.

8 Claims, 13 Drawing Sheets

(51) Int. Cl.
  *G01K 3/08* (2006.01)
  *G01N 33/38* (2006.01)
  *G01J 5/00* (2022.01)

(56) References Cited

FOREIGN PATENT DOCUMENTS

| | | |
|---|---|---|
| JP | 11-183415 | 7/1999 |
| JP | 2005-221395 | 8/2005 |
| JP | 2005221395 A * | 8/2005 |
| JP | 2005-291791 | 10/2005 |
| JP | 2007-132739 | 5/2007 |
| JP | 2012-57369 | 3/2012 |
| JP | 2016-6398 | 1/2016 |
| KR | 10-0553570 | 2/2006 |
| KR | 10-0827610 | 4/2008 |
| KR | 10-1328515 | 11/2013 |

OTHER PUBLICATIONS

Extended European Search Report for European Application No. 20830903.9, dated Jun. 16, 2023.

Written Opinion, with English translation, for International Application No. PCT/KR2020/007832, dated Sep. 18, 2020.

* cited by examiner

**RESULT OF THERMAL ANALYSIS –
EXPECTATION OF CLP SURFACE TEMPERATURE DISTRIBUTION**

| DESCRIPTION | PHOTOGRAPH | TEMPERATURE DIFFERENCE |
|---|---|---|
| OBSERVATION OF RIGHT VOID DURING POURING 100*100mm |  | 2.7°C |
| OBSERVATION OF LEFT VOID DURING POURING 100*100mm |  | 2.4°C |
| OBSERVATION OF ALL THREE VOIDS HAVING SIZE OF 300 mm X 300 mm DIRECTLY AFTER POURING IS COMPLETED |  | 2.5°C |

FIG. 9

| PHOTOGRAPHING TIME | PHOTOGRAPH | TEMPERATURE DIFFERENCE |
|---|---|---|
| 18 O'CLOCK ON DECEMBER 7TH (4 HOURS ELAPSES AFTER POURING) |  | 2.7°C |
| 21 O'CLOCK ON DECEMBER 7TH (7 HOURS ELAPSES AFTER POURING) |  | 2.3°C |
| 24 O'CLOCK ON DECEMBER 7TH (10 HOURS ELAPSES AFTER POURING) |  | 2.0°C |

FIG. 10

| PHOTOGRAPHING TIME | PHOTOGRAPH | TEMPERATURE DIFFERENCE |
|---|---|---|
| 3 O'CLOCK ON DECEMBER 8TH (13 HOURS ELAPSES AFTER POURING) |  | 3.4°C |
| 9 O'CLOCK ON DECEMBER 8TH (19 HOURS ELAPSES AFTER POURING) |  | 2.9°C |
| 15 O'CLOCK ON DECEMBER 8TH (25 HOURS ELAPSES AFTER POURING) |  | 2.8°C |

FIG. 11

| PHOTOGRAPHING TIME | PHOTOGRAPH | TEMPERATURE DIFFERENCE |
|---|---|---|
| 21 O'CLOCK ON DECEMBER 8TH (31 HOURS ELAPSES AFTER POURING, PEAK OF TEMPERATURE DIFFERENCE) |  | 5.6°C |
| 24 O'CLOCK ON DECEMBER 8TH (34 HOURS ELAPSES AFTER POURING) |  | 4.5°C |
| 12 O'CLOCK ON DECEMBER 10TH (70 HOURS ELAPSES AFTER POURING) |  | 4.0°C |

FIG. 12

| PHOTOGRAPHING TIME | PHOTOGRAPH | TEMPERATURE DIFFERENCE |
|---|---|---|
| 24 O'CLOCK ON DECEMBER 10TH | | 3.7°C |
| 12 O'CLOCK ON DECEMBER 11TH | | 2.7°C |
| 24 O'CLOCK ON DECEMBER 11TH | | 2.4°C |
| 12 O'CLOCK ON DECEMBER 12TH | | 1.9°C |

FIG. 13

| CLASSIFICATION | CONTENTS | THERMAL IMAGE |
|---|---|---|
| INITIAL OBSERVATION | TIME : 14:23<br>TEMPERATURE DIFFERENCE : 2.9°C |  |
| AFTER ADDITIONAL VIBRATION COMPACTION | TIME : 14:43<br>TEMPERATURE DIFFERENCE : 1.8°C |  |

METHOD FOR DETECTING VOID IN CONCRETE COMPOSITE MEMBER COVERED WITH STEEL PLATE USING THERMAL IMAGE, AND METHOD FOR MANAGING CONSTRUCTION OF CONCRETE COMPOSITE MEMBER COVERED WITH STEEL PLATE BY APPLYING SAME

CROSS REFERENCE TO RELATED APPLICATIONS

This application is a national entry of International Application No. PCT/KR2020/007832, filed on Jun. 17, 2020, which claims priority to Korean Patent Application No. 10-2019-0076336 under 35 U.S.C. § 119, filed on Jun. 26, 2019, the entire contents of which are hereby incorporated by reference.

TECHNICAL FIELD

The present invention relates to a method for detecting a void in a concrete composite member covered with a steel plate, and more particularly, to a method for detecting a void by sensing a temperature difference, using a thermal image, generated as heat conduction is blocked by a low thermal conductivity of the void when the void is generated in a concrete composite member covered with a steel plate.

BACKGROUND ART

An outer wall of a nuclear power plant is constructed by using a steel plate (CLP) as a mold and using a concrete composite member covered with the steel plate. However, since the steel plate mold is not removed from the concrete composite member covered with the steel plate, whether poured concrete is properly filled may not be checked by naked eyes after concrete pouring. Although vibration compaction is typically performed after the concrete pouring so that concrete is properly filled into a pouring section, a void may be generated during pouring due to various reasons such as interference with a reinforcing bar, a vertical reinforcing material, and a horizontal channel and difficulty in securing a clear view due to a pouring depth of about 3 m. When the void is generated, a steel plate may be corroded by internal moisture or weakened in strength in case of a large-sized void. Thus, the void is required to be prevented during a construction process.

Typically, presence of the void has been inspected by a difference of sounds generated when a steel plate surface is hit by, e.g., a rubber hammer. However, the typical inspection method has a limitation in precise void detection because a pouring position is not recognized in real-time due to a nuclear power plant structure, an area to be inspected by hitting of a person is limited based on an entire surface due to characteristics of a measurement method, and the inspection depends on subjective judgment on the sounds.

RELATED ART DOCUMENT (Patent document 1) KR 10-0553570 B1
(Patent document 2) KR 10-1328515 B1

DISCLOSURE OF THE INVENTION

Technical Problem

The present invention provides a method for sensing a void generated area using a thermal image during construction of a concrete composite member covered with a steel plate and detecting a void section in real time from the sensed void generated area, as a new method for detecting a void in the concrete composite member covered with the steel plate.

The present invention also provides a construction management method capable of preventing generation of a void and improving a construction quality through an additional compaction performed based on a real-time detection of a void section during construction of a concrete composite member covered with a steel plate.

Technical Solution

In accordance with an embodiment of the present invention, a method for detecting a void in a concrete composite member covered with a steel plate includes: a first step of setting, as a reference temperature difference, a temperature difference between a void and a non-void in the concrete composite member covered with the steel plate in accordance with an on-site temperature and a concrete pouring temperature; a second step of measuring the on-site temperature and the concrete pouring temperature before construction of the concrete composite member covered with the steel plate, and extracting a reference temperature difference corresponding to the on-site temperature and the concrete pouring temperature measured from the reference temperature difference set in the first step; and a third step of measuring a steel plate surface temperature of an area in which concrete is poured using a thermal image during the construction of the concrete composite member covered with the steel plate, and determining, as a void, a section in which a temperature difference between the measured steel plate surface temperature and a temperature of a surrounding part thereof is equal to or greater than the reference temperature difference extracted in the second step. Here, the on-site temperature in the first and second steps is set by a mean temperature of the steel plate surface temperature measured using the thermal image before pouring the concrete at a site or an outside air temperature at the site.

In accordance with another embodiment of the present invention, a method for managing construction of a concrete composite member covered with a steel plate includes: a first step of detecting a void of a concrete composite member covered with a steel plate during or directly after concrete pouring; and a second step of performing an additional compaction on a section that is determined as the void in the first step.

Advantageous Effects

According to the present invention, following effects may be obtained.

Firstly, since the presence of the void is determined based on the steel plate surface temperature measured using the thermal image during the construction of the concrete composite member covered with the steel plate, the void generation may be precisely expected while monitoring the temperature change through the real-time thermal image measurement, and also the void generation may be simply expected without limitation in construction position.

Secondly, the construction quality may simply improve because the void area improves by performing the additional compaction on the area in which the void is expected to be generated, and also the effective construction management may be performed because the void state is monitored over the entire construction cycle when the thermal image measurement is performed while the additional vibration compaction and the hydration reaction are performed.

MODE FOR CARRYING OUT THE INVENTION

The present invention relates to a method for detecting a void in a concrete composite member covered with a steel plate, and more particularly, to a method for detecting a void by detecting, by using a thermal image, a temperature difference generated because heat conduction is blocked by a low thermal conductivity of a void when the void is generated in the concrete composite member covered with the steel plate.

Figure 1:
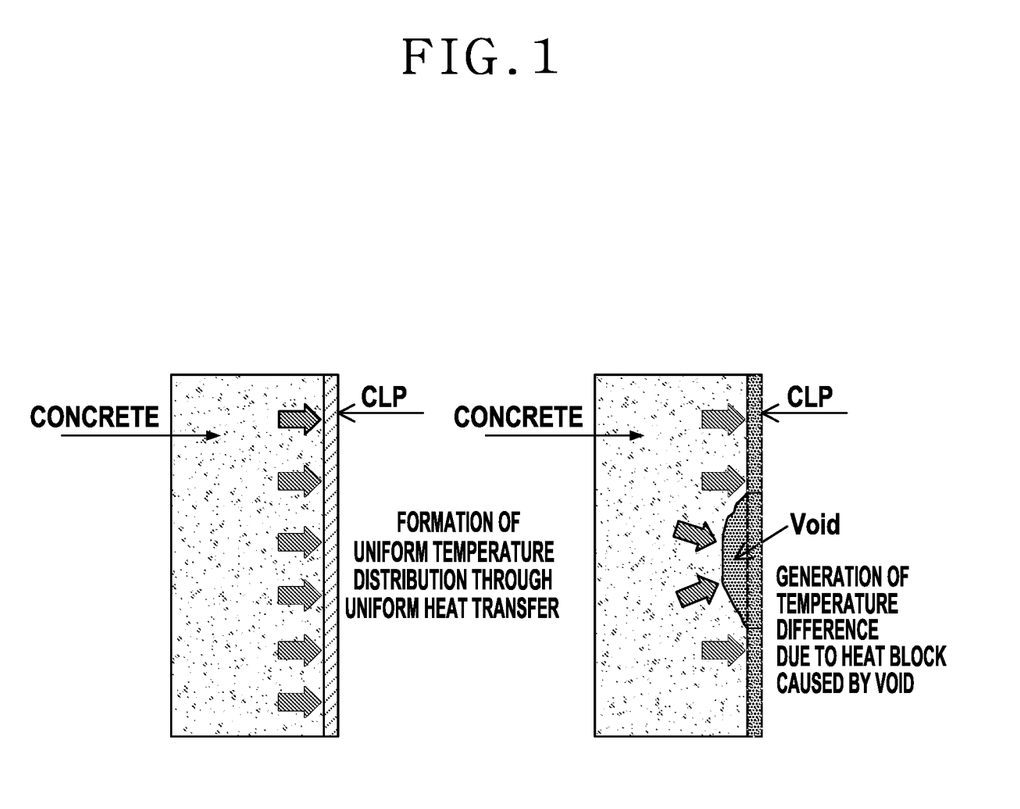
FIG. 1 is a schematic view illustrating a method for detecting a void in a concrete composite member covered with a steel plate according to the present invention.

FIG. 1 is a schematic view illustrating the method for detecting a void in a concrete composite member covered with a steel plate according to the present invention. Since a temperature difference between a void and a non-void is generated by a temperature difference between concrete and a steel plate (CLP) during concrete pouring, and the temperature difference between the void and the non-void further increases as a temperature of the concrete increases by heat of a hydration reaction after the concrete pouring, the void may be further exactly determined. Since air has a thermal conductivity of about 0.025 W/m·k and is one of the best insulation materials (an insulation performance of air gradually increases until a thickness of 20 mm by which internal convection hardly occurs), an air layer of the void serves as an insulation material when the void is generated between the steel plate (CLP) and the concrete to block heat conduction therebetween, thereby generating a temperature difference. Although a concrete temperature (internal temperature of about 60° C.) increases by the heat of the hydration reaction after the concrete pouring, a temperature difference between the void and a surrounding part thereof is generated by the insulation effect of the void. The temperature difference generated as described above may be detected by a thermal image to detect the void.

Specifically, the method for detecting a void in a concrete composite member covered with a steel plate, according to the present invention, includes: a first step of setting, as a reference temperature difference, a temperature difference between a void and a non-void in the concrete composite member covered with the steel plate in accordance with an on-site temperature and a concrete pouring temperature; a second step of measuring the on-site temperature and the concrete pouring temperature before construction of the concrete composite member covered with the steel plate, and extracting a reference temperature difference corresponding to the on-site temperature and the concrete pouring temperature measured from the reference temperature difference set in the first step; and a third step of measuring a steel plate surface temperature of an area in which concrete is poured by using a thermal image during the construction of the concrete composite member covered with the steel plate, and determining, as a void, a section in which a temperature difference between the measured steel plate surface temperature and a temperature of a surrounding part thereof is equal to or greater than the reference temperature difference extracted in the second step. Here, the on-site temperature in the first and second steps is set to be an outside air temperature at the site or an average temperature of the steel plate surface temperature measured by using the thermal image at the site before pouring concrete. The above-described detecting method is suggested as possibility of determining presence of a void is check through an electrothermal analysis simulation and a mock-up test.

The first step sets the reference temperature difference that is a criterion for determining the presence of a void. A temperature difference may be detected in accordance with a variation of a material of a surface of the steel plate (CLP) due to characteristics of the thermal image that detects infrared rays, and also various small temperature difference areas may be detected on a surface of the CLP when the thermal image is substantially photographed because various structural reinforcement materials are present on the surface of the CLP. Thus, a reference for the temperature difference to determine the presence of a void is required to detect the void, and the first step sets the reference for the temperature difference to determine the presence of the void as the reference temperature difference. However, since the temperature difference between the void (surface) and the non-void (surface) is changed in accordance with a difference between the temperature of the outside air (CLP surface temperature) and the concrete pouring temperature, the reference temperature difference is set in accordance with the on-site temperature (outside air temperature or CLP surface temperature) and the concrete pouring temperature. Preferably, the reference temperature difference may be set based on results of a thermal analysis of an abnormal state of temperatures of the void and the non-void caused by the difference between the on-site temperature and the concrete pouring temperature. When the reference temperature difference is set with reference to results of a three-dimensional transient electrothermal analysis, the reference temperature difference may be set in a range from 2° C. to 2.5° C. in case that the difference between the on-site temperature and the concrete pouring temperature is 7° C., and the reference temperature difference may be set to be a value that increases or decreases by 0.3° C. to 0.4° C. from 2° C. to 2.5° C. whenever the difference between the on-site temperature and the concrete pouring temperature increases or decreases by 1° C. from 7° C. In an experimental example 1, the thermal analysis of the abnormal state of the temperatures of the void and the non-void is performed when the on-site temperature (outside air temperature) is in a range from 0° C. to 17° C., and the concrete pouring temperature is 12° C., and the temperature difference calculated in accordance with results thereof is shown. This temperature difference may be set as the reference temperature difference.

The second and third steps determine the presence of the void during the concrete pouring at the substantial site. The second step extracts the reference temperature difference on a substantial construction site condition, and the third step determines the presence of a void section while measuring the surface temperature of the steel plate (CLP) by using the thermal image along a concrete pouring area during the concrete pouring. When the temperature difference between the surface temperature of the steel plate (CLP) and the temperature of the surrounding part thereof, which are measured during the concrete pouring, is equal to or greater than the reference temperature difference, the present of the void is determined.

When the above-described void detecting method is applied to the construction of the concrete composite member covered with the steel plate, a construction state may be easily managed, and a construction quality may improve. In other words, the construction of the concrete composite member covered with the steel plate is performed by including: the first step of detecting the void of the concrete composite member covered with the steel plate directly after the concrete is poured and compacted; and the second step of additionally compacting the section that is determined as the void in the first step. The construction quality improves by eliminating the void through the additional compaction on the section determined as the void. Here, the second step may perform the additional compaction while monitoring whether the temperature difference with the surrounding part decreases by measuring the steel plate surface temperature using the thermal image. The additional compaction may be sufficiently performed until the temperature difference with the surrounding part is within the reference temperature difference. It is checked that the temperature difference of the corresponding area decreases after the additional compaction is performed on the section in which the temperature difference is equal to or greater than the reference temperature difference and which is determined as the void when applied to the substantial site.

Furthermore, after the second step, a third step of measuring the steel plate surface temperature by using the thermal image when 24 hours elapses after the concrete pouring and monitoring the measured steel plate surface temperature while comparing the temperature difference with the surrounding part with the reference temperature difference. The temperature difference between the void and the surrounding part thereof further increases by the insulation effect of the void when 24 hours elapses after the concrete pouring although the concrete temperature increases by the heat of the hydration reaction. The presence of the void may be verified through the third step. When the section in which the reference temperature difference is abnormal is checked through the monitoring of the third step, the section may be determined as the void section and may secure the construction quality through reconstruction.

Hereinafter, the present invention will be described in detail in accordance with experimental examples. However, the following experimental examples are merely illustrative, and the scope of the present invention is not limited thereto.

[Experimental Example 1] Thermal Analysis 1 Through Simulation

Figure 2:
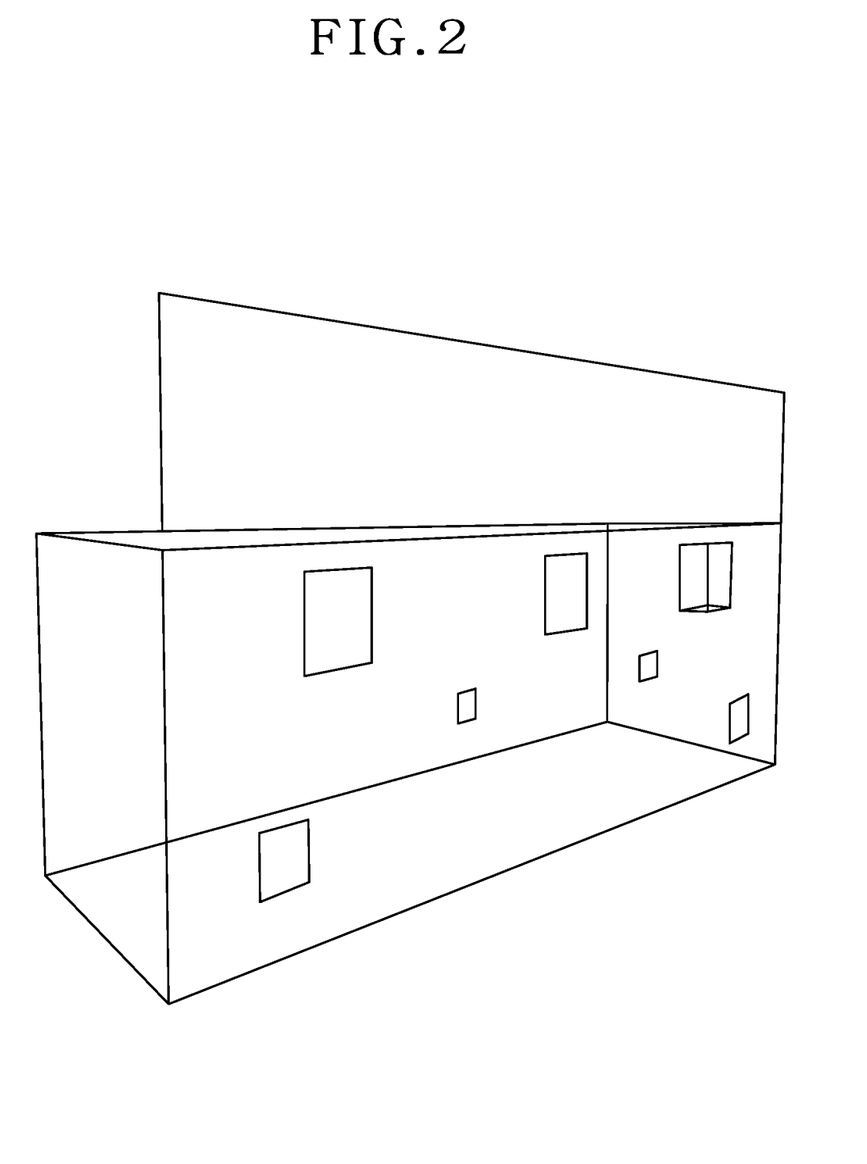
FIGS. 2 to 5 show a simulation model for setting a reference temperature difference and results of a simulation analysis according to the present invention.
Figure 3:
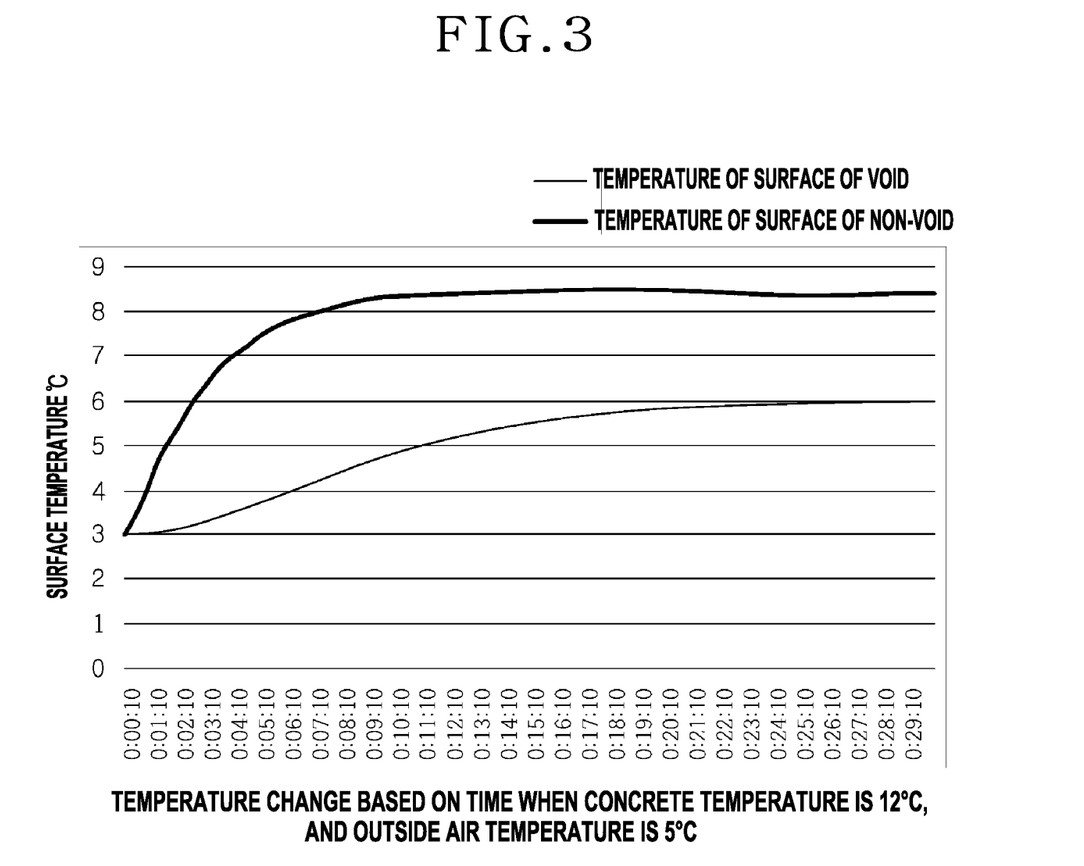

The three-dimensional transient electrothermal analysis is performed on a simulation model illustrated in FIG. 2 The analysis is performed by using PHYSIBEL Voltra 80 (dynamic thermal analysis program) by setting an input condition such that a concrete initial temperature is 12° C., pouring is performed for initial 1 minute until an upper end level, and then a natural temperature variation caused by concrete heat storage, outside temperature, and heat conduction is set to 30 minutes. Results of the thermal analysis are shown in table 1 below and FIG. 3. The table 1 and FIG. 3 are obtained by performing the analysis based on the void having a depth of 20 mm and the simulation model in FIG. 2 having a size of 300×300 mm.

TABLE 1

Results of thermal analysis

| Case | Outside air temperature (° C.) | Concrete pouring temperature (° C.) | Void surface temperature (° C.) | Non-void surface temperature (° C.) | Temperture difference (° C.) |
|---|---|---|---|---|---|
| 1 | 0 | 12 | 5.14 | 9.23 | 4.09 |
| 2 | 1 | 12 | 5.71 | 9.46 | 3.75 |
| 3 | 2 | 12 | 6.28 | 9.69 | 3.41 |
| 4 | 3 | 12 | 6.85 | 9.92 | 3.07 |
| 5 | 4 | 12 | 7.42 | 10.16 | 2.74 |
| 6 | 5 | 12 | 7.99 | 10.39 | 2.4 |
| 7 | 6 | 12 | 8.56 | 10.62 | 2.06 |
| 8 | 7 | 12 | 9.14 | 10.85 | 1.71 |
| 9 | 8 | 12 | 9.71 | 11.08 | 1.37 |
| 10 | 9 | 12 | 10.28 | 11.31 | 1.03 |
| 11 | 10 | 12 | 10.85 | 11.54 | 0.69 |
| 12 | 11 | 12 | 11.43 | 11.77 | 0.34 |
| 13 | 13 | 12 | 12.57 | 12.23 | −0.34 |
| 14 | 14 | 12 | 13.14 | 12.46 | −0.68 |
| 15 | 15 | 12 | 13.72 | 12.69 | −1.03 |
| 16 | 16 | 12 | 14.29 | 12.92 | −1.37 |
| 17 | 17 | 12 | 14.86 | 13.15 | −1.71 |

When the difference between the on-site temperature and the concrete pouring temperature is 7° C. (outside air temperature of 5° C. and concrete pouring temperature of 12° C.) as in the above table 1 and FIG. 3, it is shown that the reference temperature difference is 2.4° C. and increases or decreases by about 0.34° C. whenever the difference between the on-site temperature and the concrete pouring temperature increases or decreases by 1° C. from 7° C.

[Experimental Example 2] Thermal Analysis 2 Through Simulation

Figure 4:
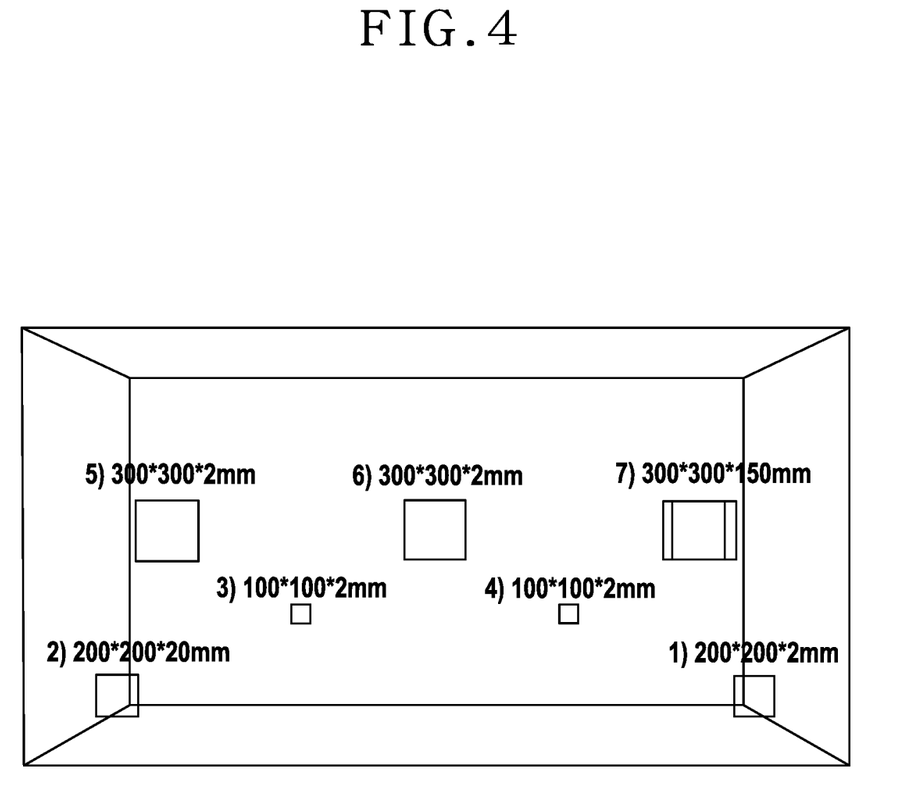

The thermal analysis is performed by using PHYSIBEL Voltra 80 (dynamic thermal analysis program) on a simulation model as illustrated in FIG. 4. An input condition is set such that a concrete initial temperature is 13° C., and an outside air temperature is 0° C., and a concrete internal temperature reaches to a peak in two days later after pouring is performed with a maximum temperature of 60° C. Results of the thermal analysis are shown in table 2 below and FIG. 5.

TABLE 2

Results of thermal analysis

| Void size (mm) | | | Temperature | Boundary with | Determining |
|---|---|---|---|---|---|
| Width × Length | Depth | No. | difference (° C.) | surrounding part | presence of void |
| 100 × 100 | 2 | 1 | 0.7 | Unclear | X |
| | 20 | 2 | 1.2 | Unclear | X |
| 200 × 200 | 2 | 3 | 2.1 | Clear | ○ |
| | 20 | 4 | 2.9 | Clear | ○ |
| 300 × 300 | 2 | 5 | 3.9 | Clear | ○ |
| | 20 | 6 | 5.1 | Clear | ○ |
| | 150 | 7 | 5.1 | Clear | ○ |

Figure 5:
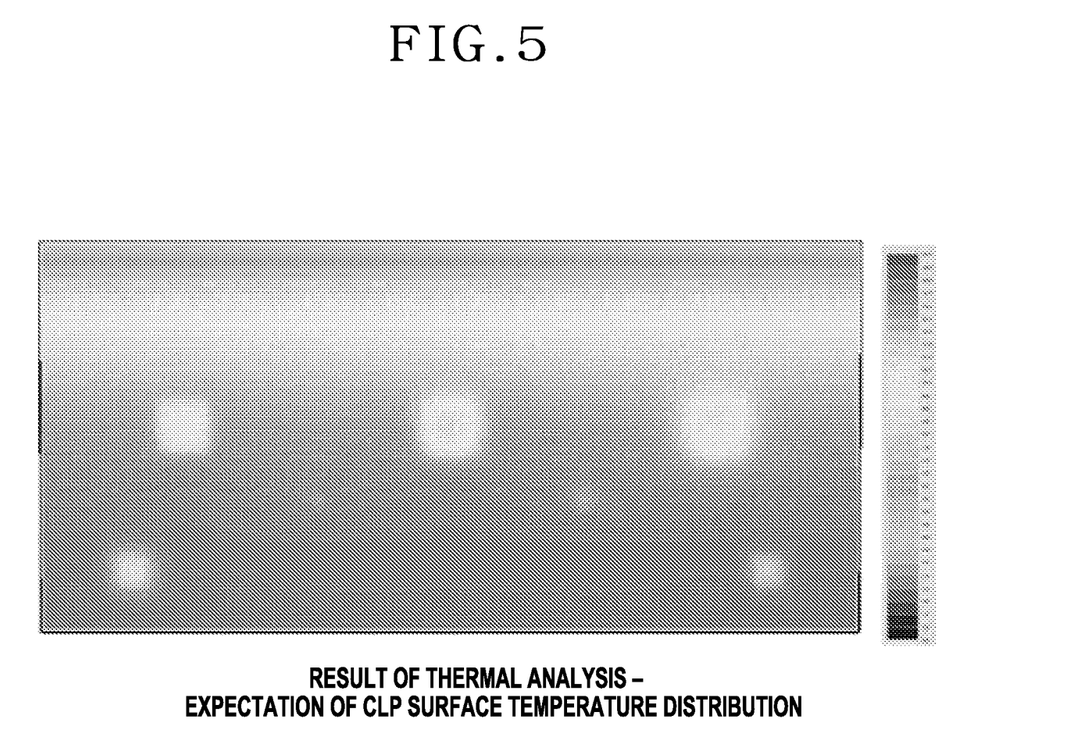

As shown in the above table 2 and FIG. 5, the void having the small size of 100 mm×100 mm shows that the temperature difference is small due to heat transfer of a surrounding part as time elapses, and a temperature boundary with the surrounding part is unclear. Thus, determining the presence of the void by the heat of the hydration reaction generated as time elapses may be difficult. In case of the void having the size of 200 mm×200 mm and the depth of 2 mm, although the boundary with the surrounding area is distinguished, since the temperature difference is about 2° C., which is slightly different from the temperature difference (about 1.5° C.) in accordance with the surface state shown when measured by using the thermal image, determining the presence of the void is required to be careful. Incase of the void having the size of 200 mm×200 mm and the depth of 20 mm, since the temperature difference is about 2.9° C., the presence of the void may be determined. The void having the size of 300 mm×300 mm may be checked by naked eyes due to the temperature difference with the surrounding part in all cases of depths from 2 mm and 150 mm, and the presence of the void may be determined.

[Experimental Example 3] Mock-Up Test

Figure 6:
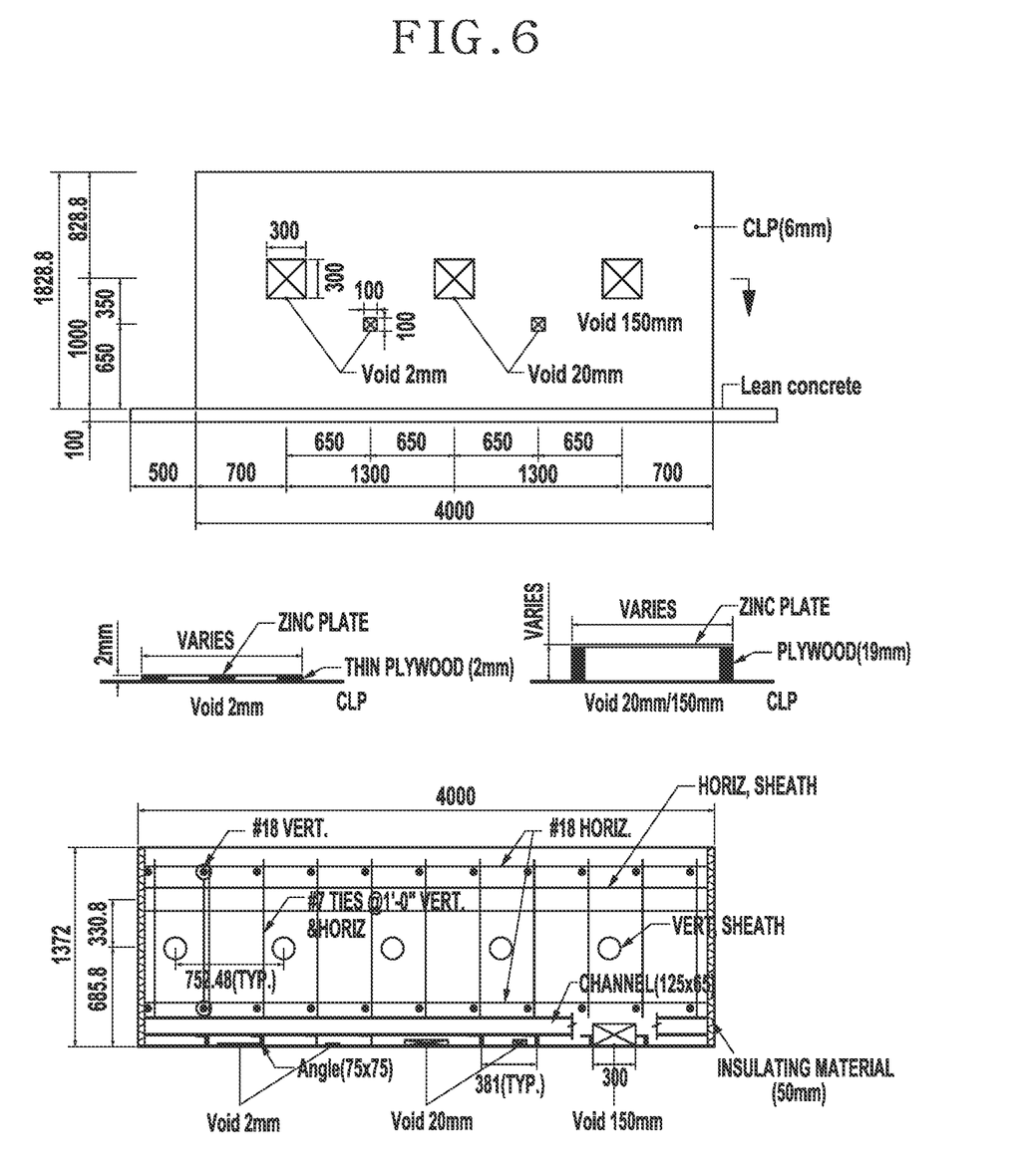
FIGS. 6 to 12 show a mock-up test specimen and observation results according to the present invention.
Figure 7:
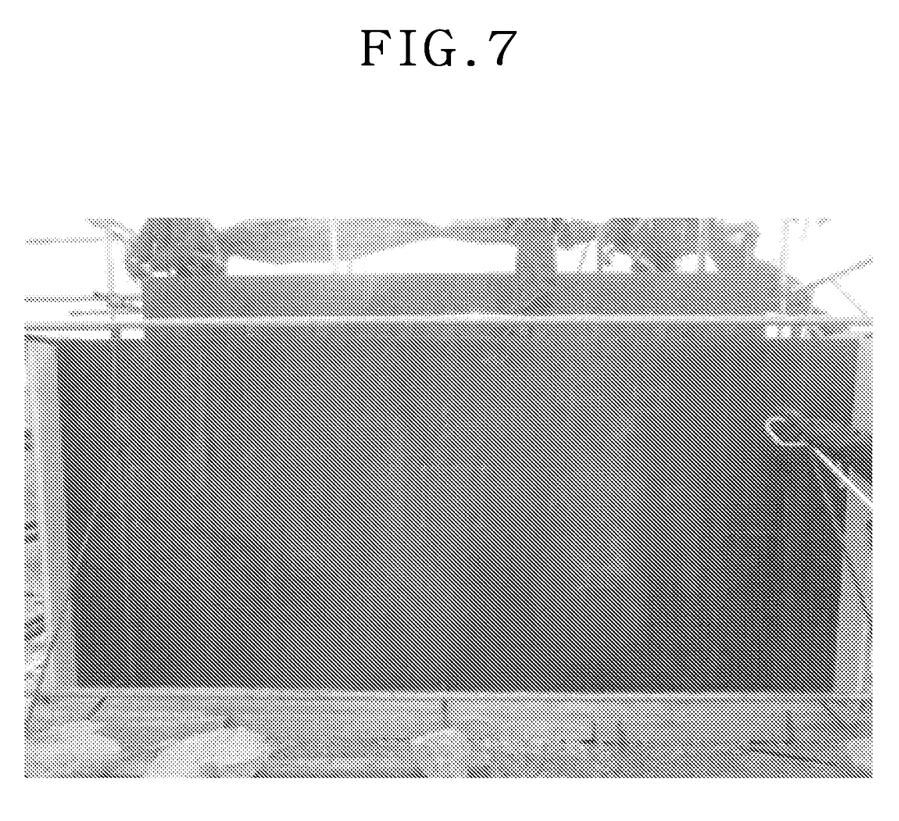

A mock-up test specimen designed as in FIG. 6 is manufactured as in FIG. 7 and observed through a thermal image thereof while pouring concrete. At the time of pouring concrete, the outside air temperature is in a range from a minimum of −1° C. to a maximum of 7° C., the average CLP surface temperature is 0.9° C., and the concrete pouring temperature is 13° C. Results of the thermal image observation are shown in FIGS. 8 to 12.

Figure 8:
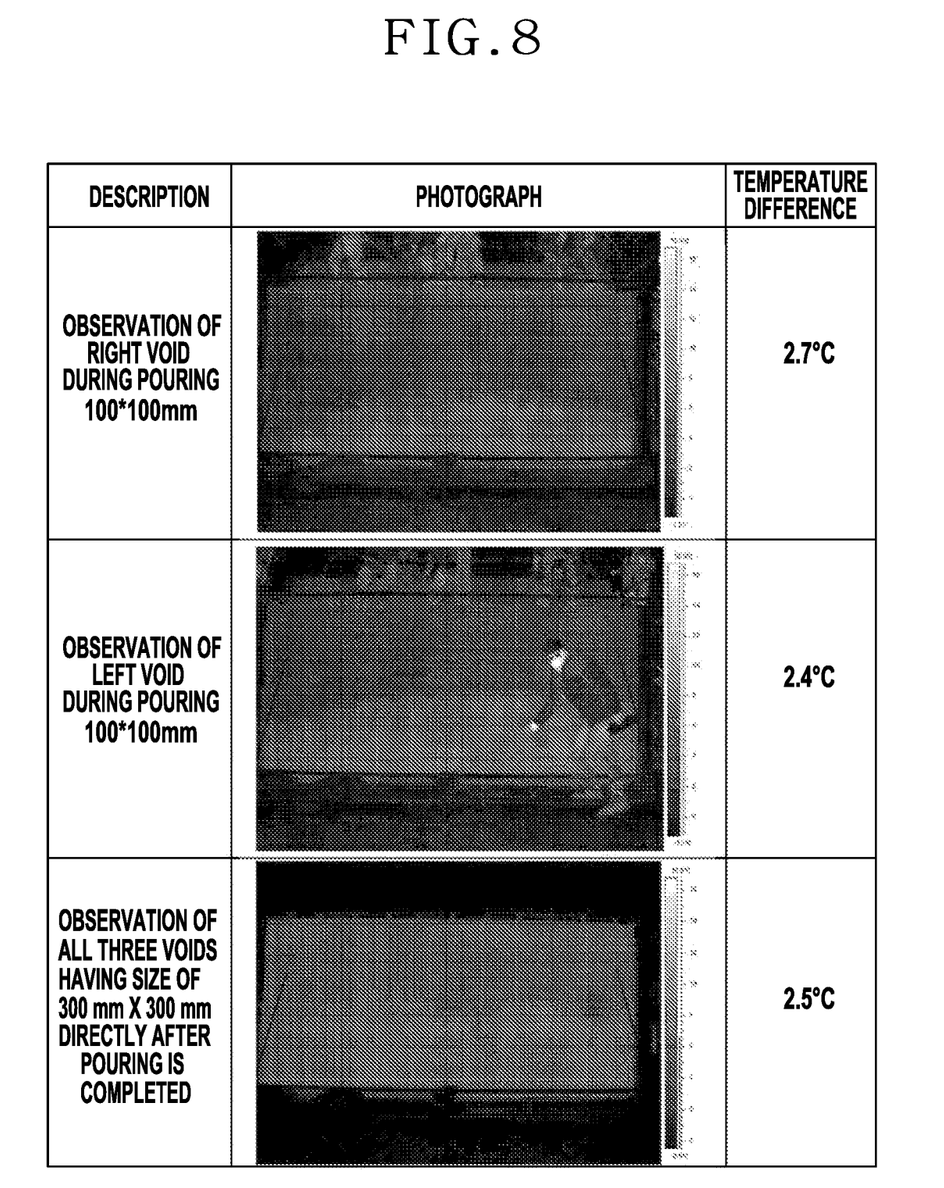
Figure 9:
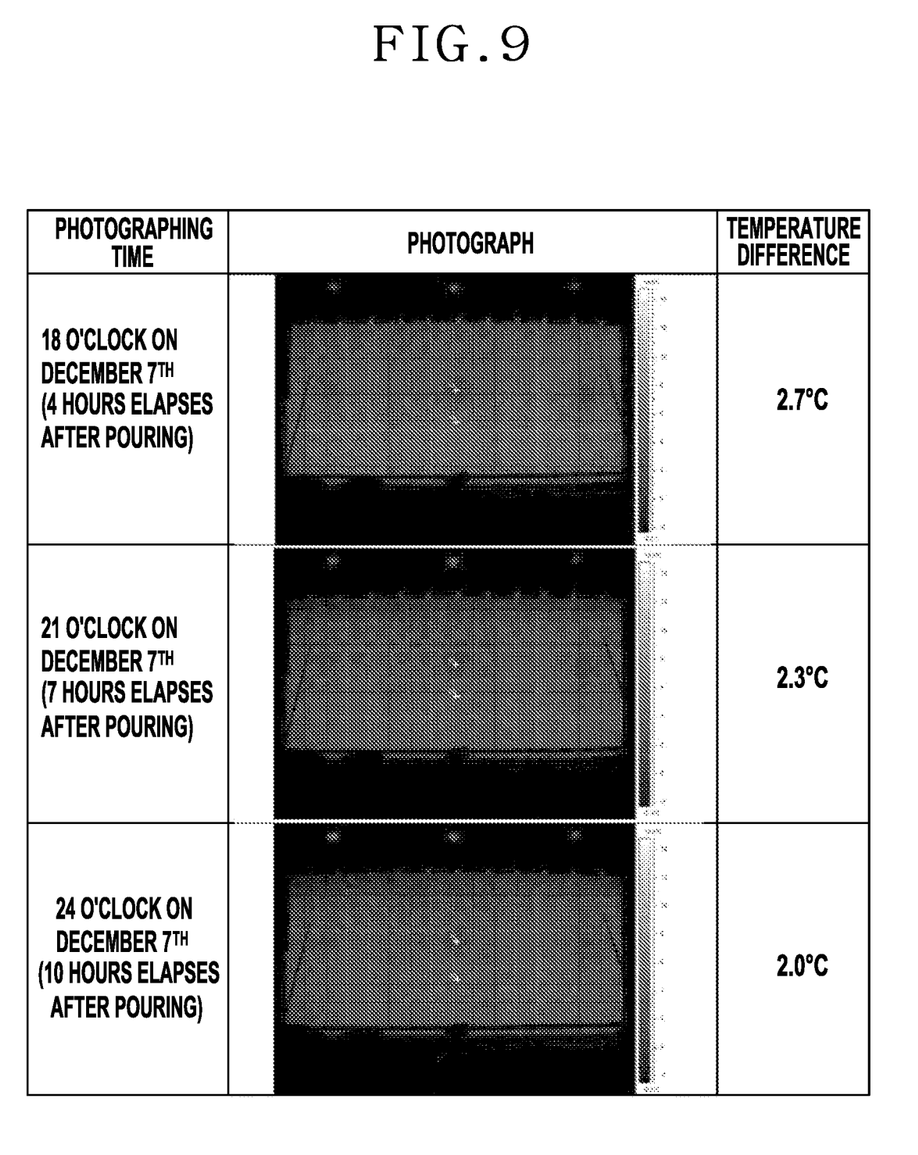
Figure 10:
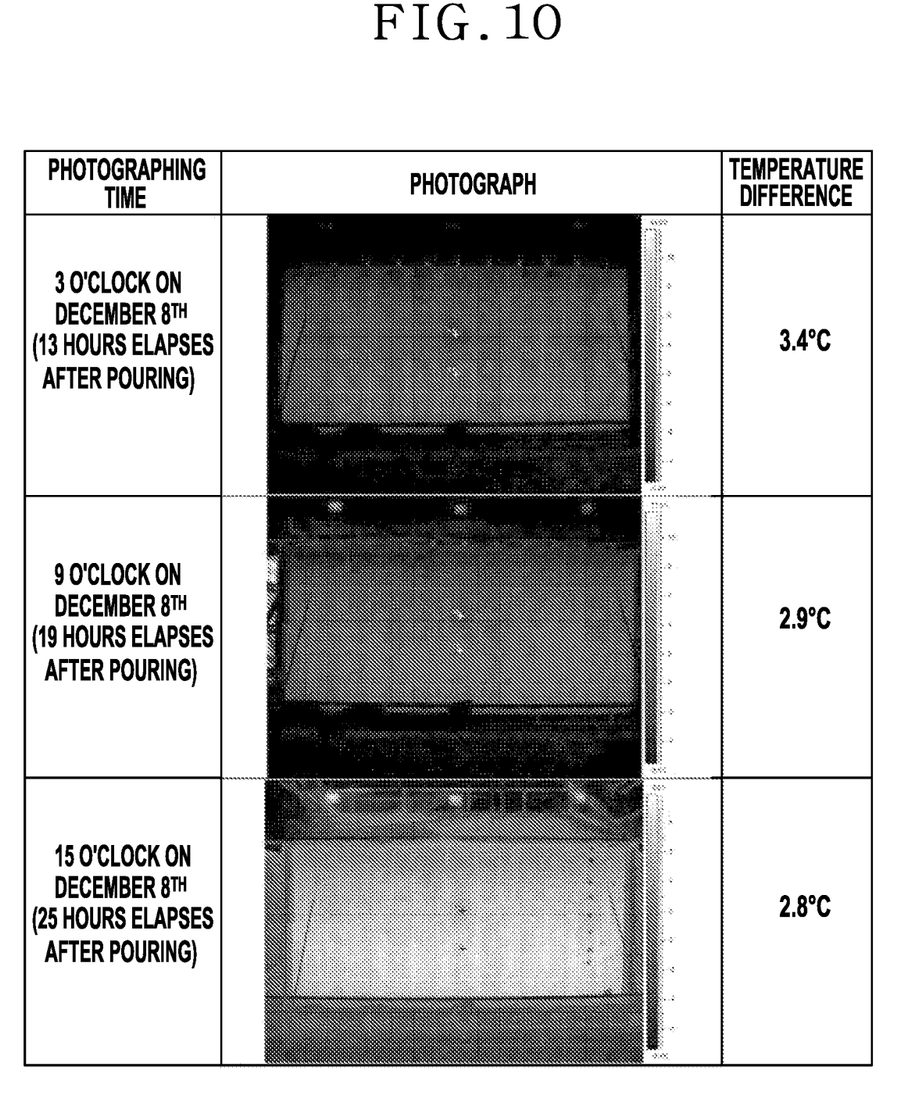
Figure 11:
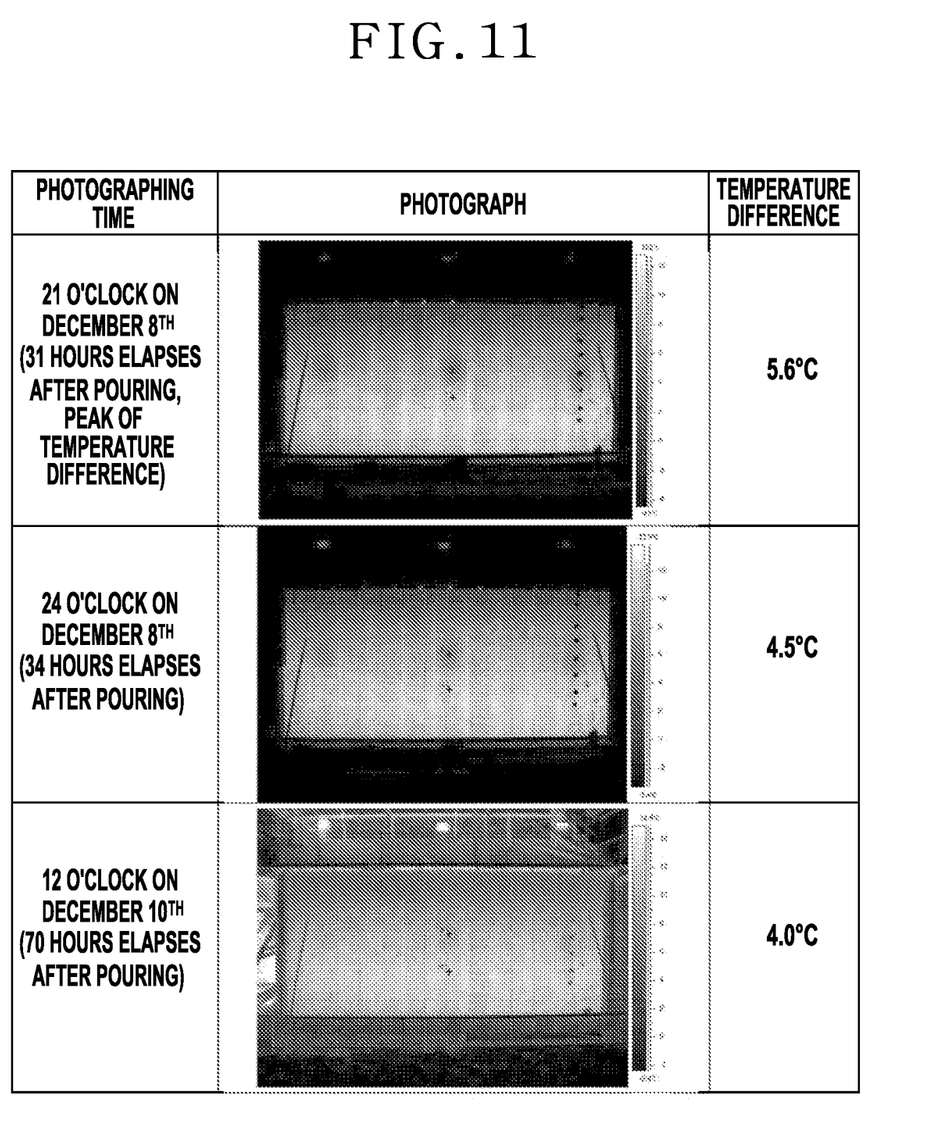
Figure 12:
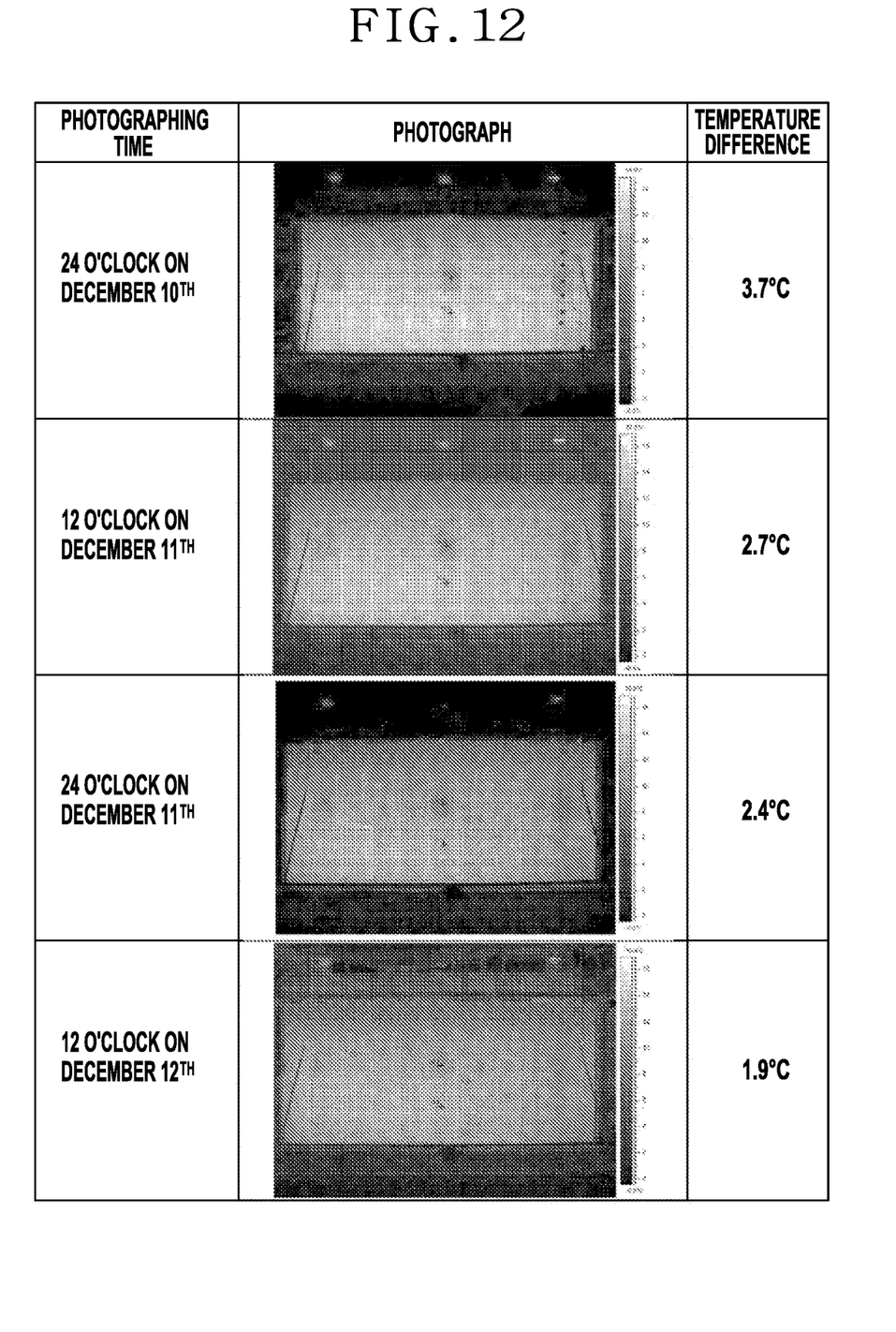

FIG. 8 shows results during the concrete pouring and directly after the concrete is poured. As shown in FIG. 8, the void having the size of 100 mm×100 mm and disposed at the right side is clearly observed as the concrete is filled during the concrete pouring, and since the temperature difference is equal to or greater than 2.4° C., the temperature difference is distinguished from the temperature difference caused by surface pollution and an angle part in the CLP on a surrounding thermal image, and thus the void is determined. However, after one to two minutes of an observation maintaining period elapses, the temperature becomes similar to the surrounding part due to heat conduction, and the shape of the void is disappeared. Since the shape of the void having the size of 300 mm×300 mm is clearly observed, and the temperature difference with the surrounding part shows high difference of about 2.5° C., the void may be determined and continuously observed even after the concrete pouring because the temperature difference is maintained.

FIGS. 9 to 12 show observation results as time elapses after the concrete pouring. The CLP surface temperature increases by the heat of the concrete hydration reaction after the concrete is poured. Thus, since the void having the size of 100 mm×100 mm is difficult to be determined as the void in the actual measurement because the temperature difference is small less than 1.1° C. due to effects of heat conduction of the surrounding part although the void is faintly observed, the void having the small size may be determined only through observation and measurement during the concrete pouring. In case of the void having the size of 300 mm×300 mm, although void observation is more difficult than during pouring until 10 hours elapses after the pouring because the hydration reaction is not sufficiently performed, and the initial concrete temperature continuously decreases. Since then, the CLP surface temperature continuously increases, and the temperature difference between the void and the non-void increases. When one day and 7 hours (31 hours) elapses after the pouring, the temperature difference increases up to 5.5° C. to record a peak, and then the temperature difference decreases to 1.9° C. when five days elapses (12 o'clock on December 12). A lower area disposed about 300 mm below from an uppermost part shows a natural temperature decrease section due to heat dissipation to outside air, and thus determining the presence of the void by using the thermal image may be difficult when the temperature difference with the outside air temperature is great. Thus, thermal image observation results during the pouring or directly after the pouring may be used as the determination reference.

[Experimental Example 4] Additional Compaction Experiment

Figure 13:
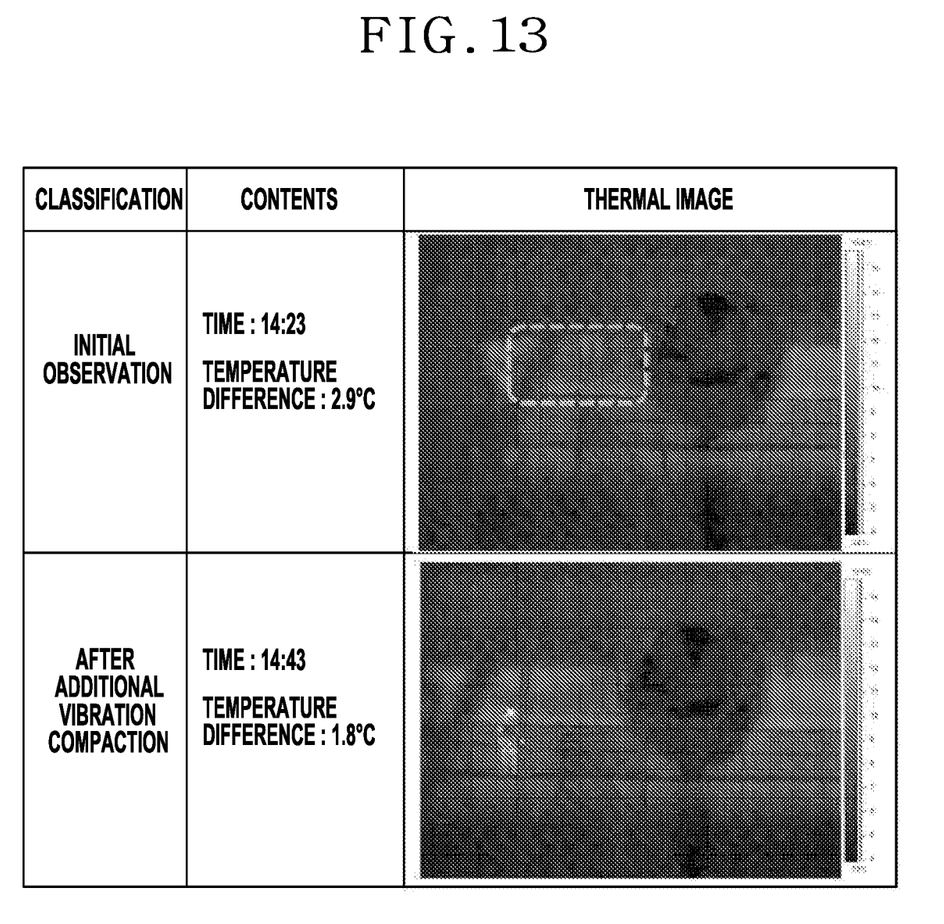
FIG. 13 shows observation results before and after additional compaction on a void section determined in an on-site experiment according to the present invention.

The temperature difference is measured while measuring by the thermal image during the concrete pouring at a nuclear power plant construction site, and then the temperature difference is measured again after vibration compaction is performed on a section in which the temperature difference is 2.9° C. Results are shown in FIG. 13, representing that the temperature difference is solved after the vibration compaction is performed.

The invention claimed is:

1. A method for detecting a void in a concrete composite member covered with a steel plate, comprising:
  a first step of setting, as a reference temperature difference, a temperature difference between a void and a non-void in the concrete composite member covered with the steel plate in accordance with an on-site temperature and a concrete pouring temperature;
  a second step of measuring the on-site temperature and the concrete pouring temperature before construction of the concrete composite member covered with the steel plate, and extracting a reference temperature difference corresponding to the on-site temperature and the concrete pouring temperature measured from the reference temperature difference set in the first step; and
  a third step of measuring a steel plate surface temperature of an area in which concrete is poured using a thermal image during the construction of the concrete composite member covered with the steel plate, and determining, as a void, a section in which a temperature difference between the measured steel plate surface temperature and a temperature of a surrounding part thereof is equal to or greater than the reference temperature difference extracted in the second step,
  wherein the on-site temperature in the first and second steps is set by a mean temperature of the steel plate surface temperature measured using the thermal image before pouring the concrete at a site or an outside air temperature at the site, and
  wherein the reference temperature difference to be a value that increases or decreases whenever a difference between the on-site temperature and the concrete pouring temperature increases or decreases.

2. The method of claim 1, wherein the first step is performed by setting the reference temperature difference in accordance with results of a heat analysis of an abnormal state of temperatures of the void and the non-void caused by the difference between the on-site temperature and the concrete pouring temperature.

3. The method of claim 2, wherein the first step sets the reference temperature difference to be in a range from 2° C. to 2.5° C. when the difference between the on-site temperature and the concrete pouring temperature is 7° C., and further the reference temperature difference to be a value that increases or decreases by 0.3° C. to 0.4° C. whenever the difference between the on-site temperature and the concrete pouring temperature increases or decreases by 1° C. from 7° C.

4. A method for managing construction of a concrete composite member covered with a steel plate by applying the method for detecting the void in the concrete composite member covered with the steel plate of claim 1, comprising:
- a first step of detecting a void of a concrete composite member covered with a steel plate during or directly after concrete pouring; and
- a second step of performing an additional compaction on a section that is determined as the void in the first step.

5. The method of claim 4, wherein the second step is performed while monitoring whether a temperature difference with a surrounding part decreases more than a reference temperature difference by measuring a steel plate surface temperature using a thermal image.

6. The method of claim 4, further comprising, after the second step, a third step of measuring a steel plate surface temperature using a thermal image when 24 hours elapses after the concrete pouring and monitoring the measured steel plate surface temperature while comparing the reference temperature difference with a temperature difference with a surrounding part.

7. A method for managing construction of a concrete composite member covered with a steel plate by applying the method for detecting the void in the concrete composite member covered with the steel plate of claim 2, comprising:
- a first step of detecting a void of a concrete composite member covered with a steel plate during or directly after concrete pouring; and
- a second step of performing an additional compaction on a section that is determined as the void in the first step.

8. A method for managing construction of a concrete composite member covered with a steel plate by applying the method for detecting the void in the concrete composite member covered with the steel plate of claim 3, comprising:
- a first step of detecting a void of a concrete composite member covered with a steel plate during or directly after concrete pouring; and
- a second step of performing an additional compaction on a section that is determined as the void in the first step.

* * * * *